US00PP21581P3

(12) United States Plant Patent
Navarro et al.

(10) Patent No.: US PP21,581 P3
(45) Date of Patent: Dec. 21, 2010

(54) MANDARIN ORANGE TREE NAMED 'SAFOR'

(50) Latin Name: *Citrus hybrida*
Varietal Denomination: Safor

(75) Inventors: Luis Navarro, Valencia (ES); José Juárez, Valencia (ES); Pablo Aleza, Valencia (ES); José Cuenca, Valencia (ES); José Manuel Julve, Valencia (ES); José Antonio Pina, Valencia (ES)

(73) Assignee: Instituto Valenciano de Investigaciones Agrarias (IVIA), Valencia (ES)

( * ) Notice: Subject to any disclaimer, the term of this patent is extended or adjusted under 35 U.S.C. 154(b) by 0 days.

(21) Appl. No.: 12/457,676

(22) Filed: Jun. 18, 2009

(65) Prior Publication Data

US 2010/0017927 P1 Jan. 21, 2010

(30) Foreign Application Priority Data

Jul. 21, 2008 (EM) ..... 20081611

(51) Int. Cl.
*A01H 5/00* (2006.01)

(52) U.S. Cl. ..... Plt./202

(58) Field of Classification Search ..... Plt./202, Plt./201
See application file for complete search history.

*Primary Examiner*—Susan B McCormick Ewoldt
(74) *Attorney, Agent, or Firm*—Buchanan Ingersoll & Rooney PC

(57) ABSTRACT

A new and distinct triploid *Citrus hybrida* cultivar is provided that is the product of controlled cross-pollination of two diploid parental plants. The new cultivar forms attractive seedless obloid-shaped, medium-late-maturing fruit with a convex base having an excellent mildly acidic flavor. The leaves are dark green in coloration. The growth habit is vigorous and erect-drooping.

2 Drawing Sheets

Botanical/commercial classification: *Citrus hybrida*/Mandarin Orange Tree.

Varietal denomination: cv. Safor.

BACKGROUND OF THE INVENTION

*Citrus* crops including Mandarin Oranges are recognized to be important to the agricultural economy in many parts of the world.

The new hybrid *Citrus* cultivar of the present invention was created during the spring of 1996 at Moncada, Valencia, Spain, when two parents were crossed which previously had been studied in the hope that they would contribute the desired characteristics required to produce quality late-ripening seedless fruit. The female parent (i.e., the seed parent) was the 'Fortune' Mandarin cultivar (non-patented in the United States). 'Fortune' is recognized to be a diploid formed by the hybridization of *C. clementina*×*C. tangerina*. The male parent (i.e., the pollen parent) was the 'Kara' Mandarin cultivar (non-patented in the United States). 'Kara' is a diploid of *C. unshiu*×*C. nobilis*. In order to achieve the cross, the anthers of the 'Kara' mandarin cultivar were removed from flowers collected during pre-anthesis and were dried in Petri dishes over silica gel in a desiccator. Dried dehisced anthers were stored in small Petri dishes at −20° C. The controlled cross-pollination was carried out by applying one anther from the male parental plant to a receptive stigma of a flower of the female parental plant. Approximately 100 flowers of the female parental plant were pollinated. From these female parental plants, 50 fruits were collected that contained 145 small seeds. Embryos numbering 134 were isolated from these seeds and were cultured in vitro. Small plants numbering 130 were recovered and were maintained. When analyzed by the use of flow cytometry, 126 of the small plants were confirmed to be triploids. The resulting triploid plants were transferred to standard potting mix and were grown under greenhouse conditions until April, 1998. Each plant next was grafted on 'Carrizo' Citrange rootstock (non-patented in the United States), which is recognized to be a cross of *C. sinensis*× *Poncinus trifoliate,* and was planted in the field for detailed evaluation. These plants first flowered during the spring of 2001, and a single plant of the present invention was selected during 2004, and was further grafted (as described) for further evaluation. The new plant initially was designated IVIA TRI 2.

It was found that the new triploid Mandarin Orange hybrid plant of the present invention displays the following combination of characteristics:

(a) displays a vigorous and erect-drooping growth habit, (b) forms dark green leaves, and (c) forms attractive easy-to-peel seedless dark orange obloid-shaped medium-late-maturing fruit having a convex base with an excellent mildly acidic flavor.

The new cultivar readily can be distinguished from its parental cultivars. More specifically, each parent plant is a diploid, unlike the triploid character of the new cultivar of the present invention.

The new cultivar also can be readily distinguished from the 'Garbi' cultivar (U.S. Plant patent application Ser. No. 12/457,675, filed concurrently herewith). The 'Garbi' cultivar displays a less erect drooping growth habit and forms fruit of late maturity whereas the present cultivar forms fruit of medium-late maturity.

The asexual reproduction of the new cultivar of the present invention by grafting on 'Carrizo' rootstock at Moncada, Valencia, Spain, has confirmed that the combination of characteristics is stable and is strictly transmissible by such asexual propagation from one generation to another. Accordingly, the new cultivar of the present invention undergoes asexual propagation in a true-to-type manner.

The new plant of the present invention has been named 'Safor'.

BRIEF DESCRIPTION OF THE PHOTOGRAPHS

The accompanying photographs show as nearly true as it is reasonably possible to make in color illustrations of this character, typical specimens of the new cultivar. The plant was grown at Moncada, Valencia, Spain, and was grafted on 'Carrizo' rootstock.

DETAILED DESCRIPTION

Figure 1:
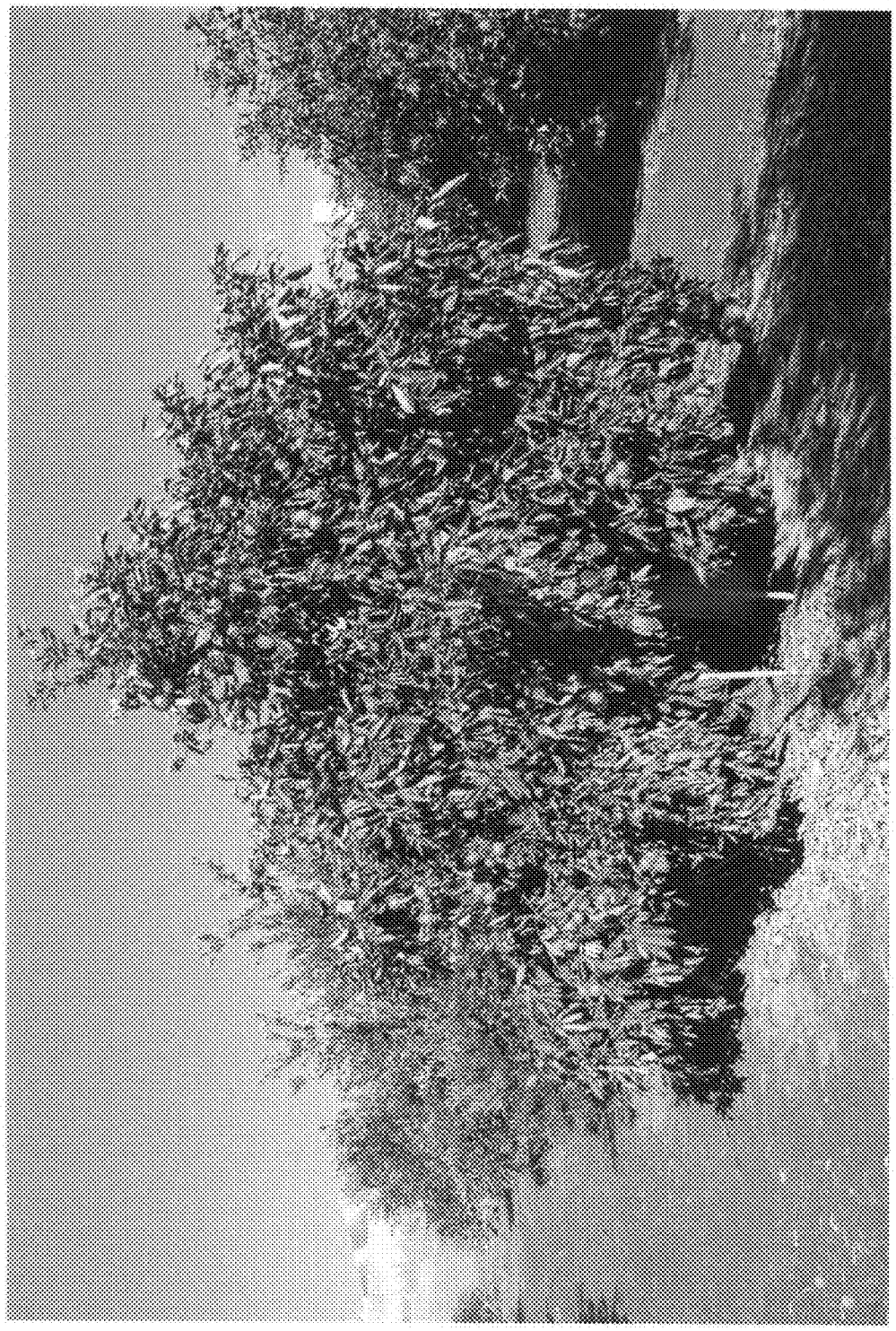
FIG. 1 illustrates a typical tree on Jan. 7, 2008 at an age of approximately three years and six months. The erect-drooping growth habit is illustrated.

The description is based on the observation of plant of the new cultivar while grafted on 'Carrizo' rootstock and growing outdoors at Moncada, Valencia, Spain. The chart used in the identification of colors is that of The Royal Horticultural Society (R.H.S. Colour Chart), London, England. Common color terms are to be accorded their customary dictionary significance.

Classification: *Citrus hybrida.*

Tree:

*Ploidy.*—Triploid.

*Growth habit.*—Vigorous, erect-drooping, and commonly obloid-ellipsoid-shaped, and similar to that of the 'Kara' male parent.

*Height.*—Commonly approximately 2.05 m on average at an age of five years.

*Width.*—Commonly approximately 2.35 m on average at an age of five years.

*Trunk diameter.*—Commonly approximately 7.8 cm on average at an age of five years measured 40 cm above the ground.

*Bark.*—Green Group 137A in coloration when young.

*Branch flexibility.*—Very flexible.

*Thorns.*—Approximately 16 mm in length on main branches, and new branches commonly bear thorns near approximately 6 percent of the buds having lengths of approximately 3.4 mm on average.

Leaves:

*Bearing.*—Evergreen.

*Size.*—Commonly approximately 13.2 cm in length on average, and approximately 4.7 cm in width on average at the widest point.

*Configuration.*—Somewhat oblong.

*Apex.*—Acute.

*Margins.*—Crenate.

*Petiole.*—Commonly approximately 14.7 mm in length on average with very small wings.

*Color.*—Dark green, Green Group 137A on the upper surface, and somewhat lighter green, Green Group 137B on the under surface.

Inflorescence:

*Time.*—Commonly during April at Moncada, Valencia, Spain.

*Type.*—Solitary in a raceme arrangement at axillary and terminal positions.

*Width.*—Approximately 3.45±0.4 cm on average.

*Petals.*—Five in number, approximately 12.7±0.7 mm in length on average, and approximately 5.3±0.3 mm in width on average.

*Color.*—White, White Group 155C.

*Stamen.*—Commonly approximately 19 to 20 in number on average, arranged separately and free, approximately 7.1±0.9 mm in size, and white in color.

*Pollen.*—Largely sterile with about 0.2 percent of the pollen grains being capable of germinating using in vitro culture during observations to date when compared to more than 82 percent for the female parent 'Fortune' Mandarin cultivar.

*Pistil.*—One in number, the ovary is generally cylindrical in shape, approximately 2.1 mm in diameter on average, and green in coloration.

*Style.*—Similar to that of the 'Fortune' and 'Kara' patental cultivars.

*Stigma.*—Similar to that of the 'Fortune' and 'Kara' parental cultivars.

Fruit:

*Time of maturity.*—Medium-late, commonly mid-February to the beginning of April at Moncada, Valencia, Spain.

*Size.*—Commonly 54.4 mm in height on average, and approximately 55 to 60 mm (i.e., approximately 59.3 mm on average) in diameter.

*Weight.*—Commonly approximately 98±28 g on average.

*Configuration.*—Obloid, substantially circular in shape in transverse section, broadest toward the distal end, absent a neck, possesses a convex base, with absence of a substantial depression at stalk end, with absence of or with few radial grooves at the stalk end, with absence of radial grooves at distal end, with absence of a collar, and somewhat flattened at distal end with the absence of a substantial depression at the distal end.

*Stylar scar.*—Small in diameter, and with no persistence of style.

*External color.*—Dark orange, near Orange Group 28B. The coloration is similar to that of 'Nova' Mandarin (non-patented in the United States) which is a cross of *C. clementina*×(*C. paradisi*×*C. tangerina*).

*Surface texture.*—Generally smooth with strong glossiness.

*Oil glands.*—More or less uniform in size with absence of pitting and pebbling and with a pleasant aroma.

*Internal flesh coloration.*—Dark orange, near Orange Group 28B.

*Rind.*—Thin, easy-to-peel, commonly approximately 2.5 mm in thickness on average, with medium adherence to the flesh, medium in strength, and medium in oiliness.

*Core.*—Commonly approximately 12.8±1 mm in diameter on average.

Figure 2:
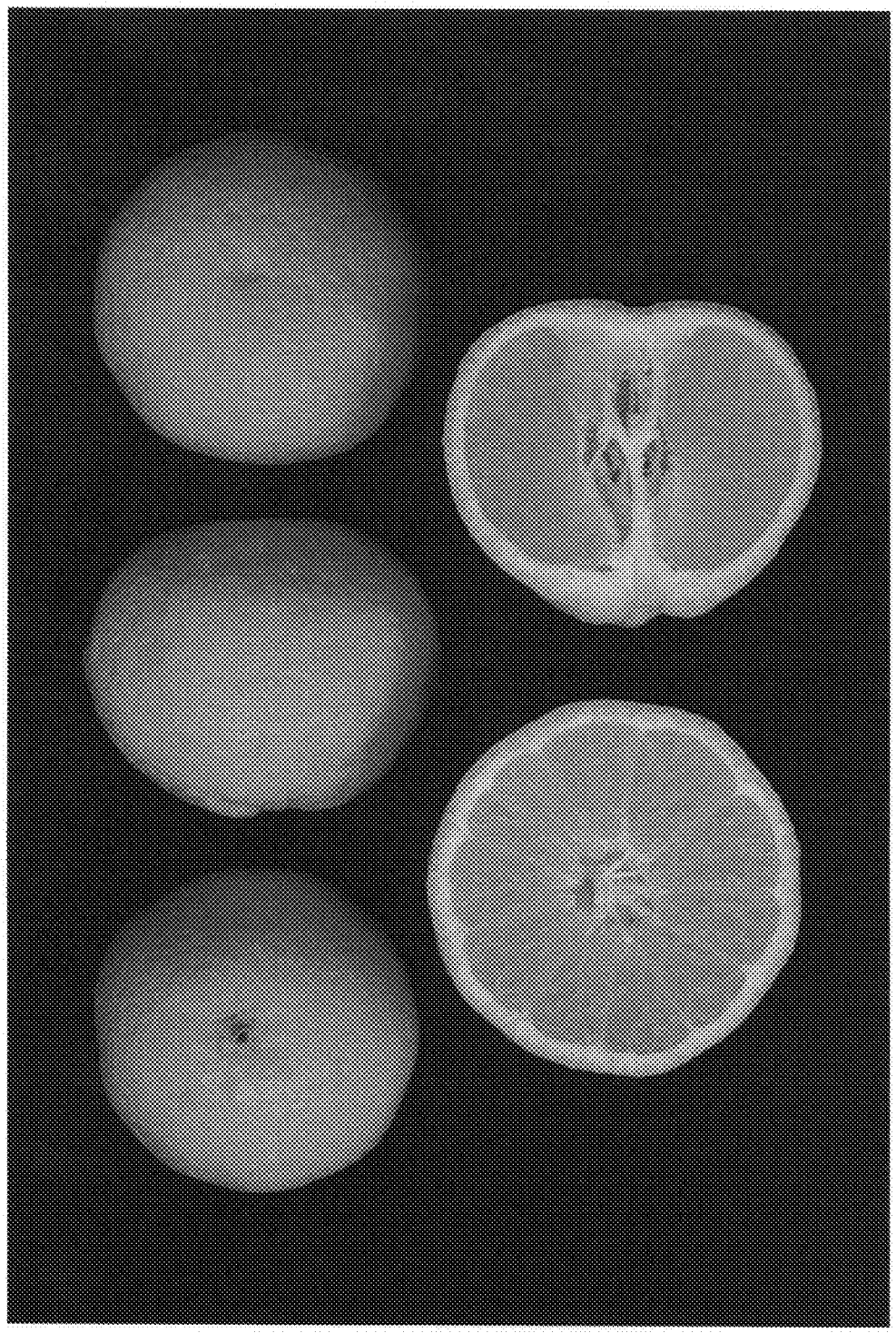
FIG. 2 illustrates typical attractive fruit on Feb. 28, 2007. The fruit flesh is shown in cross-section at the bottom and external views of the fruit are shown at the top.

*Flesh segments.*—Medium in number, commonly approximately 9 or 10 well-developed segments per fruit, with medium coherence of adjacent wall segments, with elongated juice vesicles, and with medium thickness of juice vesicles. The typical size of such segments is illustrated at the lower portion of FIG. 2.

*Navel.*—Absent or very rare.

*Parthenocarpy.*—Seedless fruit.

*Eating quality.*—Excellent with very easy eating texture of the segments.

*Juice content.*—Commonly approximately 52 percent at maturity.

*Acidity.*—Lightly acidic, with approximately 1.7 percent acid concentration at maturity, and with near 16° Brix.

*Fruit productivity.*—Similar to that of the parental 'Fortune' and 'Kara' cultivars.

Development:

*Resistance to diseases.*—During observations to date is tolerant to *Citrus Tristeza Virus* (*CTV*) and *Alternaria* spp.

*Resistance to pests.*—Is susceptible to aphids, mites, and scales that commonly are present with Mandarin Orange trees.

*Winter hardiness.*—Similar to that of the parental 'Fortune' and 'Kara' cultivars.

*Resistance to heat.*—Similar to that of the parental 'Fortune' and 'Kara' cultivars.

The new 'Safor' cultivar has not been observed under all possible environmental conditions to date. Accordingly, it is possible that the phenotypic expression may vary somewhat with changes in light intensity and duration, cultural practices, and other environmental conditions.

We claim:

1. A triploid Mandarin Orange hybrid plant having the following combination of characteristics:

(a) displays a vigorous and erect-drooping growth habit, (b) forms dark green leaves, and (c) forms attractive easy-to-peel seedless obloid-shaped dark orange medium-late-maturing fruit having a convex base with an excellent mildly acidic flavor;

substantially as herein shown and described.

* * * * *